United States Patent
Dubois et al.

(10) Patent No.: US 6,340,689 B1
(45) Date of Patent: Jan. 22, 2002

(54) METHODS OF USE OF QUINOLONE COMPOUNDS AGAINST ATYPICAL UPPER RESPIRATORY PATHOGENIC BACTERIA

(75) Inventors: Jacques Dubois, Fleuramont; Claude St-Pierre, St-Elie d'Orford, both of (CA)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/395,851

(22) Filed: Sep. 14, 1999

Related U.S. Application Data

(60) Provisional application No. 60/141,409, filed on Jun. 29, 1999, and provisional application No. 60/141,457, filed on Jun. 29, 1999.

(51) Int. Cl.[7] .......................................... A61K 31/4375
(52) U.S. Cl. ...................................................... 514/300
(58) Field of Search .......................................... 514/300

(56) References Cited

FOREIGN PATENT DOCUMENTS

| EP | 0 688 772 A | 12/1995 |
| WO | WO 98/42705 | 10/1998 |

OTHER PUBLICATIONS

Dubois, et al., "In Vitro Activity of Gatifloxacin, Compared with Ciprofloxacin, Clarithromycin, Erythromycin, and Rifampin, against Legionella Species," *Diagnostic Microbiology and Infectious Disease*, 33: 261–265 (1999).

Edelstein, "Antimicrobial Chemotherapy for Legionnaires' Disease: A Review," *Clinical Infectious Diseases*, 21(S3): S265–S276 (1995).

Murray, et al., "Manual of Clinical Microbiology," ASM Press, 6th ed., 533–544 (1995).

Dubois, et al., "In vitro activity, postantibiotic effect and human monocyte activity of grepafloxacin against Legionella species," *Clinical Microbiology and Infection*, 5: 205–212 (1999).

Craig, et al., "Postantibiotic Effect," Antibiotics in Laboratory Medicine, 3rd Edition, 403–431 (1991).

Horwitz, "Interactions Between *Legionella pneumophila* and Human Mononuclear Phagocytes," ASM Press: 159–166 (1984).

Jorgensen, et al., "Methods for Dilution Antimicrobial Susceptibility Tests for Bacteria That Grow Aerobically," NCCLS, 17(2) M7–A4: 1–86 (1997).

Kelly, et al. "SB–265805: A Potent New Quinolone," *ICAAC*, San Diego Convention Centre, 105–F Poster Session: 1–41 (1998).

Ruckdeschel et al., Journal of Antimicrobial Chemotherapy, vol. 43 (suppl. B), 25–29 (May 1, 1999).*

J–I. Oh et al., "In vitro and In vivo Antibacterial Activities of LB20304, a New fluoronaphthyridone," *Abstracts of the 35th ICAAC*, p. 148, S–122, Abst F205 (1995).

Y–K. Kim et al., "Synthesis and Antibacterial Activities of LB203204: A New Fluoronaphthyridone Antibiotic Containing Novel Oxime Functionalized Pyrrolidine," *Abstracts of the 35th ICAAC*, p. 148, S–122, Abst F204 (1995).

G. Cormican, "Comparative Antimicrobial and Spectrum Activity of LB20304a, a New Fluoronated Naphthyridone Compound", *Abstracts of the 36th ICAAC*, 109 Abst F53 (1996).

Kelly et al., "Antipneumococcal Activity of SB 265805 (A New Broad Spectrum Quinolone) Compared with Nine Compounds by MIC," 38th ICAAC, San Diego CA, Abst F–87, p. 254 (1998).

* cited by examiner

Primary Examiner—Phyllis G. Spivack
(74) Attorney, Agent, or Firm—Loretta J. Henderson; Edward R. Gimmi; William T. King

(57) ABSTRACT

A method of treating an atypical upper respiratory pathogenic bacteria comprising administering a gemifloxacin compound is disclosed.

9 Claims, No Drawings

METHODS OF USE OF QUINOLONE COMPOUNDS AGAINST ATYPICAL UPPER RESPIRATORY PATHOGENIC BACTERIA

This application claims benefit of Provisionals applications No. 60/141,409 filed Jun. 29, 1999 and 60/141,457, filed Jun. 29, 1999.

This invention relates, in part, to methods of using quinolone antibiotics, particularly a gemifloxacin compound, against atypical upper respiratory pathogenic bacteria.

BACKGROUND OF THE INVENTION

Quinolones have been shown to be effective to varying degrees against a range of certain respiratory tract pathogens. However, as diseases caused by these pathogens are on the rise, there exists a need for antimicrobial compounds that are more potent and that exhibit a longer post-antibiotic effect than the present group of quinolones.

Gemifloxacin mesylate (SB-265805) is a novel fluoroquinolone useful as a potent antibacterial agent. Gemifloxacin compounds are described in detail in patent application PCT/KR98/00051 published as WO 98/42705. Patent application EP 688772 discloses novel quinoline(naphthyridine) carboxylic acid derivatives, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of formula I.

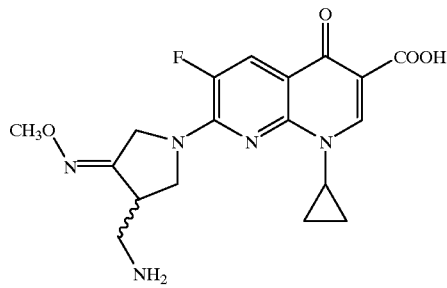

I

PCT/KR98/00051 discloses (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

Provided herein is an invention based, in part, on a significant discovery made using a gemifloxacin compound against a range of variety of Legionella isolated from nosocomial or acquired respiratory tract infections and from environmental sources, demonstrating the activity of the gemifloxacin compound used was superior to a number of quinolones as described in more detail herein. Gemifloxacin compounds are valuable compounds for the treatment of diseases caused by or related to atypical respiratory tract pathogens, thereby filling an unmet medical need.

SUMMARY OF THE INVENTION

An object of the invention is a method for modulating metabolism of atypical upper respiratory pathogenic bacteria comprising the step of contacting atypical upper respiratory pathogenic bacteria with an antibacterially effective amount of a composition comprising a gemifloxacin compound, or an antibacterially effective derivative thereof.

A further object of the invention is a method wherein said atypical upper respiratory pathogenic bacteria is selected from the group consisting of: a member of the genus Legionella, a member of the genus, Pseudomonas, *Pseudomonas aeruginosa* strain, a *Legionella pneumophila* strain, a *Legionella pneumophila* serogroup 1, a *Legionella pneumophila* serogroup 2, a *Legionella pneumophila* serogroup 3, a *Legionella pneumophila* serogroup 4, a *Legionella pneumophila* serogroup 5, a *Legionella pneumophila* serogroup 6, a *Legionella pneumophila* serogroup 7, a *Legionella pneumophila* serogroup 8, a *Legionella dumoffii* strain, a *Legionella longbeacheae* strain, a *Legionella micdadei* strain, a *Legionella oakridgensis* strain, a *Legionella feelei* strain, a *Legionella anisa* strain, a *Legionella sainthelensi* strain, a *Legionella bozemanii* strain, a *Legionella gormanii* strain, a *Legionella wadsworthii* strain, a *Legionella jordanis* strain and a *Legionella gormanii* strain.

Also provided by the invention is a method of treating or preventing a bacterial infection by atypical upper respiratory pathogenic bacteria comprising the step of administering an antibacterially effective amount of a composition comprising a gemifloxacin compound to a mammal suspected of having or being at risk of having an infection with atypical upper respiratory pathogenic bacteria.

A preferred method is provided wherein said modulating metabolism is inhibiting growth of said bacteria or killing said bacteria.

A further preferred method is provided wherein said contacting said bacteria comprises the further step of introducing said composition into a mammal, particularly a human.

Further preferred methods are provided by the invention wherein said bacteria is selected from the group consisting of: a member of the genus Legionella, a member of the genus, Pseudomonas, *Pseudomonas aeruginosa* strain, a *L. pneumophila* strain, a *L. pneumophila* serogroup 1, a *L. pneumophila* serogroup 2, a *L. pneumophila* serogroup 3, a *L. pneumophila* serogroup 4, a *L. pneumophila* serogroup 5, a *L. pneumophila* serogroup 6, a *L. pneumophila* serogroup 7, a *L. pneumophila* serogroup 8, a *L. dumoffii* strain, a *L. longbeacheae* strain, a *L. micdadei* strain, a *L. oakridgensis* strain, a *L. feelei* strain, a *L. anisa* strain, a *L. sainthelensi* strain, a *L. bozemanii* strain, a *L. gormanii* strain, a *L. wadsworthii* strain, a *L. jordanis* strain and a *L. gormanii* strain.

A further embodiment of the invention is method for modulating metabolism of atypical upper respiratory pathogenic bacteria comprising the step of contacting atypical upper respiratory pathogenic bacteria with an antibacterially effective amount of a composition comprising a compound selected from the group consisting of: gemifloxacin, ofloxacin, levofloxacin, trovafloxacin, azithromycin, moxifloxacin, ciprofloxacin, clarithromycin, rifampicin and erythromycin; or an antibacterially effective derivative of any of these compounds.

A still further embodiment of the invention is a method of treating or preventing a bacterial infection by atypical upper respiratory pathogenic bacteria comprising the step of administering an antibacterially effective amount of a composition comprising a compound selected from the group consisting of: gemifloxacin, ofloxacin, levofloxacin, trovafloxacin, azithromycin, moxifloxacin, ciprofloxacin, clarithromycin, rifampicin and erythromycin; or an antibacterially effective derivative of any of these compounds, to a mammal suspected of having or being at risk of having an infection with atypical upper respiratory pathogenic bacteria.

It is preferred in the methods of the invention that said contacting is performed once daily.

Various changes and modifications within the spirit and scope of the disclosed invention will become readily apparent to those skilled in the art from reading the following descriptions and from reading the other parts of the present disclosure.

DESCRIPTION OF THE INVENTION

The present invention provides, among other things, methods for using a composition comprising a gemifloxacin compound against atypical upper respiratory pathogenic bacteria, especially a member of the genus Legionella, a member of the genus, Pseudomonas, Pseudomonas aeruginosa strain, a L. pneumophila strain, a L. pneumophila serogroup 1, a L. pneumophila serogroup 2, a L. pneumophila serogroup 3, a L. pneumophila serogroup 4, a L. pneumophila serogroup 5, a L. pneumophila serogroup 6, a L. pneumophila serogroup 7, a L. pneumophila serogroup 8, a L. dumoffii strain, a L. longbeacheae strain, a L. micdadei strain, a L. oakridgensis strain, a L. feelei strain, a L. anisa strain, a L. sainthelensi strain, a L. bozemanii strain, a L. gormanii strain, a L. wadsworthii strain, a L. jordanis strain or a L. gormanii strain.

As used herein "gemifloxacin compound(s)" means a compound having antibacterial activity described in patent application PCT/KR98/00051 published as WO 98/42705, or patent application EP 688772.

This invention was based, in part, on analyses evaluating the in vitro activity and postantibiotic effect (herein "PAE") of gemifloxacin compared with those of trovafloxacin, moxifloxacin, grepafloxacin, levofloxacin, ofloxacin, ciprofloxacin, azithromycin, clarithromycin, erythromycin and rifampicin against isolates of Legionella pneumophila and other Legionella spp. Test isolates included L. pneumophila serogroup 1–12 (204), L. dumoffii (10), L. micdadei (10) and L. longbeacheae (7). The PAE was determined by exposing the isolates to the test antimicrobials for 1 hour at four times the minimum inhibitory concentration (herein "MIC"). The antimicrobial was removed by three consecutive centrifugations into fresh broth. The PAE was calculated by measuring bacterial growth kinetics in similar antimicrobial-free cultures. Rifampicin and trovafloxacin were the most active agents tested ($MIC_{90} \leq 0.008$ mg/L). Gemifloxacin displayed high potency ($MIC_{90}$ 0.016 mg/L) which was comparable to levofloxacin, grepafloxacin and moxifloxacin ($MIC_{90}$ 0.016 mg/L) and more active than ciprofloxacin and ofloxacin ($MIC_{90}$ 0.03 mg/L). Against L. dumoffii and L. longbeachae, gemifloxacin ($MIC_{90}$ 0.06 mg/L) was as active than ciprofloxacin, ofloxacin, grepafloxacin and moxifloxacin. Against erythromycin-resistant L. pneumophila, gemifloxacin showed the longest PAE at 4.65 hours, compared with 4.18 hours for grepafloxacin, 3.38 hours for moxifloxacin and 2.83 hours for trovafloxacin. The gemifloxacin PAE was significantly superior to that of rifampicin (0.9 h), clarithromycin (1.9 h) and levofloxacin (2.59 h). Against erythromycin-susceptible L. pneumophila only gemifloxacin, moxifloxacin, levofloxacin, ofloxacin and ciprofloxacin had a PAE over 3 hours. For erythromycin-resistant Legionella spp. other than L. pneumophila, gemifloxacin, moxifloxacin, levofloxacin and ofloxacin had PAEs in excess of 3 hour, which was significantly longer than the PAE of ciprofloxacin grepafloxacin and erythromycin. The half-life for gemifloxacin and the data presented here indicate a significant PAE to support a once-daily administration of this agent for the treatment of Legionella infections, and this dosing is preferred in the methods of the invention.

The MIC range of gemifloxacin against L. pneumophila serogroups 1–9 was 0.008–0.06 mg/L (Tables 2 and 3). Gemifloxacin was 5–6-fold more active than erythromycin against L. pneumophila strains tested. Gemifloxacin activity against L. pneumophila strains was higher than ciprofloxacin and ofloxacin but similar to grepafloxacin and moxifloxacin.

*L. pneumophila* strains of serogroups 1–3 and 7–9 were more susceptible to gemifloxacin than *L. pneumophila* serogroups 4–6. Against the most frequent *L. pneumophila*, such as serogroup 1, gemifloxacin $MIC_{90}$ (0.016 mg/L) was superior to azithromycin, clarithromycin, erythromycin, ofloxacin and ciprofloxacin.

Against *L. dumoffii* and *L. longbeacheae*, gemifloxacin, grepafloxacin and clarithromycin showed superior activity to azithromycin and erythromycin (Table 4). Against *L. micdadei*, gemifloxacin, ciprofloxacin, ofloxacin and moxifloxacin MICs were 5-fold more active than erythromycin.

Against erythromycin-resistant *L. pneumophila* only gemifloxacin, moxifloxacin and grepafloxacin displayed a mean PAE of >3 hours (Table 5). Clarithromycin, erythromycin and rifampicin showed a PAE of <2 hours against these strains. Against erythromycin-resistant Legionella spp. other than *pneumophila*, gemifloxacin, grepafloxacin, levofloxacin, ofloxacin and rifampicin displayed a mean PAE of >3 hours, and erythromycin and clarithromycin of <2 hours.

Against erythromycin-susceptible *L. pneumophila*, gemifloxacin, moxifloxacin, ofloxacin and ciprofloxacin displayed a mean PAE of >3 hours. Gemifloxacin and ofloxacin were the only quinolones showing a mean PAE of >2 hours against erythromycin-susceptible Legionella spp. other than *L. pneumophila*.

Gemifloxacin is an effective antimicrobial agent against most Legionella spp. and was significantly superior to the commonly used legionellosis therapy, erythromycin.

Against erythromycin-susceptible *L. pneumophila*, the mean PAE of gemifloxacin (3.49 hours) was ≧1 h longer than that of trovafloxacin, levofloxacin and clarithromycin.

Against erythromycin-susceptible Legionella spp. other than *pneumophila* the mean PAE of gemifloxacin (2.27 hours) was ≧1 h longer than that of trovafloxacin, moxifloxacin and clarithromycin.

Against erythromycin-resistant *L. pneumophila*, the mean PAE of gemifloxacin (4.65 hours) was significantly superior to the mean PAE of trovafloxacin, levofloxacin, ciprofloxacin, azithromycin, clarithromycin, erythromycin and rifampicin. A difference in mean PAE was also noted between gemifloxacin and trovafloxacin against Legionella spp. other than *L. pneumophila*.

The results of this study indicate that gemifloxacin should be a promising agent for the treatment of lower respiratory tract infections caused by Legionella spp.

TABLE 1

Legionella Strains Tested

| Microrganism | No. of strains tested |
|---|---|
| *L. pneumophila* | 204* |
| *L. micdadei* | 10 |
| *L. dumoffii* | 10 |
| *L. longbeacheae* | 7 |
| Others† | 7 |

*10 different serogroups

†*oakridgensis, feelei, anisa, sainthelensi, bozemanii, gormanii, wadsworthii*

TABLE 2

Susceptibility of *Legionella pneumophila* Serogroups 1–4

| | *L. pneumophila* serogroup 1 (n = 85) MIC (mg/L) | | | *L. pneumophila* serogroup 2 (n = 17) MIC (mg/L) | | |
|---|---|---|---|---|---|---|
| Antimicrobial | Range | 50% | 90% | Range | 50% | 90% |
| Gemifloxacin | 0.008–0.06 | 0.016 | ≦0.004 | 0.008–0.016 | 0.008 | 0.016 |
| Trovafloxacin | ≦0.004–0.016 | ≦0.004 | ≦0.004 | ≦0.004 | ≦0.004 | ≦0.004 |
| Moxifloxacin | ≦0.004–0.03 | 0.016 | 0.016 | ≦0.004–0.016 | 0.008 | 0.008 |
| Grepafloxacin | ≦0.004–0.06 | 0.016 | 0.016 | ≦0.004–0.03 | 0.008 | 0.016 |
| Levofloxacin | ≦0.004–0.016 | 0.016 | 0.016 | ≦0.004–0.016 | 0.008 | 0.008 |
| Ofloxacin | 0.008–0.03 | 0.03 | 0.03 | 0.008–0.03 | 0.016 | 0.03 |
| Ciprofloxacin | 0.016–0.25 | 0.03 | 0.03 | ≦0.004–0.03 | 0.016 | 0.016 |
| Azithromycin | 0.008–1.0 | 0.06 | 0.5 | 0.008–0.12 | 0.06 | 0.12 |
| Clarithromycin | ≦0.004–0.12 | 0.06 | 0.06 | ≦0.004–0.06 | 0.03 | 0.06 |
| Erythromycin | 0.03–1.0 | 0.25 | 1.0 | 0.008–0.5 | 0.25 | 0.25 |
| Rifampicin | ≦0.004–0.008 | ≦0.004 | 0.008 | ≦0.004 | ≦0.004 | ≦0.004 |
| | *L. pneumophila* serogroup 3 (n = 15) MIC (mg/L) | | | *L. pneumophila* serogroup 4 (n = 26) MIC (mg/L) | | |
| Antimicorbial | Range | 50% | 90% | Range | 50% | 90% |
| Gemifloxacin | 0.008–0.016 | 0.016 | 0.016 | 0.008–0.03 | 0.016 | 0.03 |
| Trovafloxacin | ≦0.004 | ≦0.004 | ≦0.004 | ≦0.004 | ≦0.004 | ≦0.004 |
| Moxifloxacin | ≦0.004–0.016 | 0.008 | 0.016 | ≦0.004–0.016 | 0.016 | 0.016 |
| Grepafloxacin | ≦0.004–0.016 | 0.008 | 0.016 | 0.008–0.016 | 0.008 | 0.016 |
| Levofloxacin | 0.008–0.016 | 0.008 | 0.016 | 0.004–0.016 | 0.016 | 0.016 |
| Ofloxacin | 0.016–0.03 | 0.016 | 0.03 | 0.008–0.03 | 0.03 | 0.03 |
| Ciprofloxacin | ≦0.004–0.03 | 0.03 | 0.03 | 0.016–0.12 | 0.03 | 0.06 |
| Azithromycin | 0.016–0.25 | 0.12 | 0.25 | 0.008–0.25 | 0.12 | 0.12 |
| Clarithromycin | 0.016–0.06 | 0.03 | 0.06 | 0.004–0.06 | 0.03 | 0.06 |
| Erythromycin | 0.06–0.5 | 0.25 | 0.5 | 0.016–0.5 | 0.5 | 0.5 |
| Rifampicin | ≦0.004 | ≦0.004 | ≦0.004 | ≦0.004–0.008 | ≦0.004 | ≦0.004 |

TABLE 3

Susceptibility of *L. pneumophila* Serogroups 5–12

| | *L. pneumophila* serogroup 5 (n = 15) MIC (mg/L) | | | *L. pneumophila* serogroup 6 (n = 40) MIC (mg/L) | | |
|---|---|---|---|---|---|---|
| Antimicrobial | Range | 50% | 90% | Range | 50% | 90% |
| Gemifloxacin | 0.03–0.06 | 0.03 | 0.03 | 0.008–0.03 | 0.016 | 0.03 |
| Trovafloxacin | ≦0.004–0.008 | ≦0.004 | ≦0.004 | ≦0.004 | ≦0.004 | ≦0.004 |
| Moxifloxacin | ≦0.004–0.03 | 0.016 | 0.016 | ≦0.004–0.016 | 0.008 | 0.016 |
| Grepafloxacin | ≦0.004–0.003 | 0.016 | 0.03 | ≦0.004–0.016 | 0.008 | 0.016 |
| Levofloxacin | ≦0.004–0.016 | 0.008 | 0.016 | 0.008–0.016 | 0.008 | 0.016 |
| Ofloxacin | 0.008–0.03 | 0.016 | 0.03 | 0.008–0.03 | 0.03 | 0.03 |
| Ciprofloxacin | 0.016–0.06 | 0.03 | 0.03 | ≦0.004–0.03 | 0.03 | 0.03 |
| Azithromycin | 0.008–0.5 | 0.03 | 0.25 | 0.016–0.25 | 0.06 | 0.12 |
| Clarithromycin | 0.03–0.06 | 0.03 | 0.06 | ≦0.004–0.06 | 0.016 | 0.06 |
| Erythromycin | 0.06–1.0 | 0.25 | 0.5 | 0.008–0.25 | 0.12 | 0.25 |
| Rifampicin | ≦0.004 | ≦0.004 | ≦0.004 | ≦0.004–0.008 | ≦0.004 | ≦0.004 |
| | *L. pneumophila* serogroup 7 (n = 2) MIC (mg/L) | | | *L. pneumophila* serogroup 8, 9 (n = 4) MIC (mg/L) | | |
| Antimicrobial | Range | 50% | 90% | Range | 50% | 90% |
| Gemifloxacin | 0.008–0.016 | 0.008 | 0.016 | 0.016 | 0.016 | 0.016 |
| Trovafloxacin | ≦0.004 | ≦0.004 | ≦0.004 | ≦0.004 | ≦0.004 | ≦0.004 |
| Moxifloxacin | ≦0.004–0.016 | ≦0.004 | 0.016 | 0.016 | 0.016 | 0.016 |
| Grepafloxacin | ≦0.004–0.008 | ≦0.004 | 0.008 | 0.008 | 0.008 | 0.008 |
| Levofloxacin | 0.008–0.016 | 0.008 | 0.016 | 0.008–0.016 | 0.008 | 0.016 |
| Ofloxacin | 0.03 | 0.03 | 0.03 | 0.03 | 0.03 | 0.03 |
| Ciprofloxacin | 0.03 | 0.03 | 0.03 | 0.03 | 0.03 | 0.03 |

TABLE 3-continued

Susceptibility of *L. pneumophila* Serogroups 5–12

| | | | | | | |
|---|---|---|---|---|---|---|
| Azithromycin | 0.06 | 0.06 | 0.06 | 0.06 | 0.06 | 0.06 |
| Clarithromycin | 0.016–0.06 | 0.016 | 0.06 | 0.06 | 0.06 | 0.06 |
| Erythromycin | 0.12–0.5 | 0.12 | 0.5 | 0.25 | 0.25 | 0.25 |
| Rifampicin | ≦0.004 | ≦0.004 | ≦0.004 | ≦0.004 | ≦0.004 | ≦0.004 |

TABLE 4

Susceptibility of Legionella Other Than *pneumophila*

| | *L. dumoffii* (n = 10) MIC (mg/L) | | | *L. micadadei* (n = 10) MIC (mg/L) | | |
|---|---|---|---|---|---|---|
| Antimicrobial | Range | 50% | 90% | Range | 50% | 90% |
| Gemifloxacin | 0.06 | 0.06 | 0.06 | 0.008–0.03 | 0.016 | 0.03 |
| Trovafloxacin | ≦0.004–0.008 | 0.008 | 0.008 | ≦0.004 | ≦0.004 | ≦0.004 |
| Moxifloxacin | 0.008–0.03 | 0.03 | 0.03 | 0.008–0.03 | 0.016 | 0.03 |
| Grepafloxacin | 0.06 | 0.06 | 0.06 | ≦0.004–0.016 | 0.008 | 0.016 |
| Levofloxacin | 0.016 | 0.016 | 0.016 | 0.008–0.016 | 0.016 | 0.016 |
| Ofloxacin | 0.03 | 0.03 | 0.03 | 0.03 | 0.03 | 0.03 |
| Ciprofloxacin | 0.016–0.03 | 0.016 | 0.03 | 0.016–0.03 | 0.016 | 0.03 |
| Azithromycin | 0.12–0.25 | 0.12 | 0.25 | 0.016–0.25 | 0.25 | 0.25 |
| Clarithromycin | 0.03–0.06 | 0.03 | 0.06 | 0.03–0.12 | 0.06 | 0.06 |
| Erythromycin | 0.25–0.5 | 0.25 | 0.5 | 0.25–1 | 0.5 | 1 |
| Rifampicin | ≦0.004–0.03 | 0.008 | 0.016 | 0.008 | 0.008 | 0.008 |
| | *L. longbeacheae* (n = 7) MIC (mg/L) | | | Other Legionella spp. (n = 7)* MIC (mg/L) | | |
| Antimicrobial | Range | 50% | 90% | Range | 50% | 90% |
| Gemifloxacin | 0.016–0.06 | 0.06 | 0.06 | 0.016–0.06 | 0.03 | 0.06 |
| Trovafloxacin | ≦0.004 | ≦0.004 | ≦0.004 | ≦0.004 | ≦0.004 | ≦0.004 |
| Moxifloxacin | 0.008–0.03 | 0.016 | 0.03 | 0.008–0.03 | 0.008 | 0.03 |
| Grepafloxacin | ≦0.004–0.06 | 0.03 | 0.06 | ≦0.004–0.03 | 0.03 | 0.03 |
| Levofloxacin | 0.008–0.016 | 0.016 | 0.016 | 0.008–0.06 | 0.016 | 0.016 |
| Ofloxacin | 0.016–0.03 | 0.03 | 0.03 | ≦0.004–0.06 | 0.016 | 0.06 |
| Ciprofloxacin | ≦0.004–0.03 | 0.016 | 0.03 | ≦0.004–0.03 | 0.016 | 0.03 |
| Azithromycin | 0.016–0.25 | 0.12 | 0.25 | 0.016–0.5 | 0.12 | 0.5 |
| Clarithromycin | 0.008–0.06 | 0.06 | 0.06 | ≦0.004–0.12 | 0.03 | 0.12 |
| Erythromycin | 0.008–0.5 | 0.25 | 0.5 | 0.016–1 | 0.5 | 1 |
| Rifampicin | ≦0.004–0.06 | ≦0.004 | 0.06 | ≦0.004–0.008 | ≦0.004 | 0.008 |

*Includes one isolates of *L. bozemanii*, *L. feelei*, *L. jordanis*, *L. gormanii*, *L. oakridgensis*, *L. sainthelensi* and *L. wadsworthii*.

TABLE 5

Mean PAE of Antimicrobials Against
Erythromycin-resistant and -susceptible Strains of Legionella

| | Mean PAE (h)* | | | |
|---|---|---|---|---|
| | Erythromycin-resistant strains | | Erythromycin-susceptible strains | |
| Antimicrobial (4 × MIC) | *L. pneumophila* (n = 7) | Legionella spp.† (n = 9) | *L. pneumophila* (n = 15) | Legionella spp.** (n = 13) |
| Gemifloxacin | 4.65 ± 3 | 3.34 ± 2 | 3.49 ± 3 | 2.27 ± 2 |
| Trovafloxacin | 2.83 ± 2 | 2.25 ± 2 | 1.71 ± 1 | 1.22 ± 1 |
| Moxifloxacin | 3.38 ± 2 | 2.02 ± 1 | 3.59 ± 3 | 1.18 ± 2 |
| Grepafloxacin | 4.18 ± 3 | 3.67 ± 1 | 2.62 ± 3 | 1.67 ± 1 |
| Levofloxacin | 2.59 ± 2 | 3.24 ± 1 | 2.14 ± 2 | 1.35 ± 1 |
| Ofloxacin | 2.99 ± 1 | 4.13 ± 2 | 3.53 ± 3 | 3.04 ± 2 |
| Ciprofloxacin | 2.86 ± 2 | 2.13 ± 3 | 3.61 ± 2 | 1.86 ± 2 |

TABLE 5-continued

Mean PAE of Antimicrobials Against
Erythromycin-resistant and -susceptible Strains of Legionella

| | Mean PAE (h)* | | | |
|---|---|---|---|---|
| | Erythromycin-resistant strains | | Erythromycin-susceptible strains | |
| Antimicrobial (4 × MIC) | *L. pneumophila* (n = 7) | Legionella spp.† (n = 9) | *L. pneumophila* (n = 15) | Legionella spp.** (n = 13) |
| Azithromycin | 2.16 ± 1 | 2.13 ± 1 | 2.91 ± 3 | 1.86 ± 2 |
| Clarithromycin | 1.90 ± 1 | 1.60 ± 2 | 0.72 ± 2 | 0.98 ± 2 |
| Erythromycin | 0.90 ± 1 | 0.44 ± 1 | 0.93 ± 1 | 2.06 ± 2 |
| Rifampicin | 0.93 ± 4 | 5.6 ± 3 | 2.86 ± 5 | 3.09 ± 4 |

*Means are given ± SD
†*L. micdadei* (n = 1), *L. dumofii* (n = 3), *L. bozemanii* (n = 1), *L. wadsworthii* (n = 1), *L. jordanis* (n = 1), *L. longbeacheae* (n = 2)
**L. micdadei* (n = 4), *L. dumofii* (n = 5), *L. bozemanii* (n = 1), *L. gormanii* (n = 1), *L.jordanis* (n = 1), *L. longbeacheae* (n = 1)

The invention provides a method for modulating metabolism of atypical upper respiratory pathogenic bacteria. Skilled artisans can readily choose atypical upper respiratory pathogenic bacteria or patients infected with or suspected to be infected with these organisms to practice the methods of the invention. Alternatively, the bacteria useful in the methods of the invention may be those described herein.

The contacting step in any of the methods of the invention may be performed in many ways that will be readily apparent to the skilled artisan. However, it is preferred that the contacting step comprises provision of a composition comprising a gemifloxacin compound to a mammal, particularly a human patient in need of such composition or directly to bacteria in culture medium or buffer or on a surface.

For example, when contacting a human patient or contacting said bacteria in a human patient or in vitro, the compositions comprising a gemifloxacin compound, preferably pharmaceutical compositions may be administered in any effective, convenient manner including, for instance, administration by topical, oral, anal, vaginal, intravenous, intraperitoneal, intramuscular, subcutaneous, intranasal or intradermal routes among others.

It is also preferred that these compositions be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a compound of the invention, preferably a gemifloxacin compound, and a pharmaceutically acceptable carrier or excipient. Such carriers may include, but are not limited to, saline, buffered saline, dextrose, water, glycerol, ethanol and combinations thereof. The formulation should suit the mode of administration.

Gemifloxacin compounds and compostions of the methods of the invention may be employed alone or in conjunction with other compounds, such as bacterial efflux pump inhibtor compounds or antibiotic compounds, particularly non-quinolone compounds, e.g., beta-lactam antibiotic compounds.

In therapy or as a prophylactic, the active agent of a method of the invention is preferably administered to an individual as an injectable composition, for example as a sterile aqueous dispersion, preferably an isotonic one.

Alternatively, the gemifloxacin compounds or compositions in the methods of the invention may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the antibacterially effective amount is a daily dosage level of the active agent from 0.001 mg/kg to 10 mg/kg, typically around 0.1 mg/kg to 1 mg/kg, preferably about1 mg/kg. A physician, in any event, will determine an actual dosage that is most suitable for an individual and will vary with the age, weight and response of the particular individual. The above dosages are exemplary of the average case. There can, of course, be individual instances where higher or lower dosage ranges are merited, and such are within the scope of this invention. It is preferred that the dosage is selected to modulate metabolism of the bacteria in such a way as to inhibit or stop growth of said bacteria or by killing said bacteria. The skilled artisan may identify this amount as provided herein as well as using other methods known in the art, e.g. by the application MIC tests.

A further embodiment of the invention provides for the contacting step of the methods to further comprise contacting an in-dwelling device in a patient. In-dwelling devices include, but are not limited to, surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A gemifloxacin compound or composition of the invention may be administered by injection to achieve a systemic effect against relevant bacteria, preferably a atypical upper respiratory pathogenic bacteria, shortly before insertion of an in-dwelling device. Treatment may be continued after surgery during the in-body time of the device. In addition, the composition could also be used to broaden perioperative cover for any surgical technique to prevent bacterial wound infections caused by or related to atypical upper respiratory pathogenic bacteria.

In addition to the therapy described above, a gemifloxacin compound or composition used in the methods of this invention may be used generally as a wound treatment agent to prevent adhesion of bacteria to matrix proteins, particularly atypical upper respiratory pathogenic bacteria, exposed in wound tissue and for prophylactic use in dental treatment as an alternative to, or in conjunction with, antibiotic prophylaxis.

Alternatively, a gemifloxacin compound or composition of the invention may be used to bathe an indwelling device immediately before insertion. The active agent will preferably be present at a concentration of 1 µg/ml to 10 mg/ml for bathing of wounds or indwelling devices.

Also provided by the invention is a method of treating or preventing a bacterial infection by atypical upper respiratory pathogenic bacteria comprising the step of administering an antibacterially effective amount of a composition comprising a gemifloxacin compound to a mammal, preferably a human, suspected of having or being at risk of having an infection with atypical upper respiratory pathogenic bacteria.

While a preferred object of the invention provides a method wherein said atypical upper respiratory pathogenic bacteria is selected from the group consisting of: a member of the genus Legionella, a member of the genus, Pseudomonas, *Pseudomonas aeruginosa* strain, a *L. pneumophila* strain, a *L. pneumophila* serogroup 1, a *L. pneumophila* serogroup 2, a *L. pneumophila* serogroup 3, a *L. pneumophila* serogroup 4, a *L. pneumophila* serogroup 5, a *L. pneumophila* serogroup 6, a *L. pneumophila* serogroup 7, a *L. pneumophila* serogroup 8, a *L. dumoffii* strain, a *L. longbeacheae* strain, a *L. micdadei* strain, a *L. oakridgensis* strain, a *L. feelei* strain, a *L. anisa* strain, a *L. sainthelensi* strain, a *L. bozemanii* strain, a *L. gormanii* strain, a *L. wadsworthii* strain, a *L. jordanis*; strain and a *L. gormanii* strain. Other atypical upper respiratory pathogenic bacteria may also be included in the methods. The skilled artisan may identify these organisms as provided herein as well as using other methods known in the art, e.g. MIC tests.

Preferred embodiments of the invention include, among other things, methods wherein said composition comprises gemifloxacin, or a pharmaceutically acceptable derivative thereof.

EXAMPLES

The present invention is further described by the following examples. The examples are provided solely to illustrate the invention by reference to specific embodiments. This exemplification's, while illustrating certain specific aspects of the invention, do not portray the limitations or circumscribe the scope of the disclosed invention.

All examples were carried out using standard techniques, which are well known and routine to those of skill in the art, except where otherwise described in detail.

All parts or amounts set out in the following examples are by weight, unless otherwise specified.

Example 1

Bacterial Strains

A variety of Legionella were isolated from respiratory tract and environmental sources. Identification of organisms was by standard methods know in the art (for example, see, Washington, C. W. Jr. Legionella. In: Murray et al., eds. *Manual of Clinical Microbiology.* 6th ed. American Society of Microbiology 1995: 533–544).

Example 2

Susceptibility Testing

MICs were determined by standard 2-fold agar dilution procedure using Buffered Yeast Extract agar (herein "BYE") (National Committee for Clinical Laboratory Standards: Methods for antimicrobial susceptibility tests for bacteria that growth aerobically, approved standards M 7-A4. National Committee for Laboratory Standards, Villanova, Pa, 1997).

A final innoculum of about $10^4$ colony forming units (herein "CFU") was inoculated onto the BYE containing doubling dilutions of antibiotics (0.004–256 mg/L). Plates were incubated at 35° C. for 48 hours. An MIC was defined as the lowest concentration of antimicrobial that completely inhibited visible growth. Strains of *Pseudomonas aeruginosa* ATCC 27853 and *L. pneumophila* ATCC 33152 were included as controls.

Example 3

Determination of PAE

The in vitro method using the broth technique (Craig, W. A. *Antibiotics in laboratory medicine*. Williams & Wilkins 1986: 515–536) was used to determine the PAE with Buffered Yeast extract (BYE). Each strain was exposed to antimicrobial concentration of four times the MIC. Fresh inoculum (1 ml, final concentration of $10^6$–$10^7$ CFU/ml) was added to 9 ml of prepared antimicrobial containing medium and to 9 ml of drug-free control medium and incubated at 37° C. for 1–2 hours. Antimicrobial agent was removed by three consecutive centrifugations at 1200×g for 10 minutes. Counts of CFU/ml were performed on all cultures at time zero, before and after washing, and every 1 hour until turbidity develops. The counts of CFU/ml were graphed and the duration of PAE was calculated by equation:

$$PAE=T-C$$

where T is the time required for the count of CFU in the test culture to increase 1 $\log_{10}$ above the count observed immediately after drug removal, and C is the time required for the count of untreated control culture to increase by 1 $\log_{10}$ above the count observed immediately after the completion of the same procedure used on the test culture for drug removal.

Each reference cited herein is hereby incorporated by reference in its entirety. Moreover, each patent application to which this application claims priority is hereby incorporated by reference in its entirety.

What is claimed is:

1. A method for modulating metabolism of an atypical upper respiratory pathogexnic bacteria comprising the step of contacting atypical upper respiratory pathogenic bacteria with an antibacterially effective amount of a composition comprising a gemifloxacin compound, or an antibacterially effective derivative thereof, and wherein said atypical, upper respiratory pathogenic bacteria is selected from the group consisting of: a *L. dumoffii* strain, a *L. longbeacheae* strain, a *L. micdadei* strain, a *L. oakridgensis* strain, a *L. feelei* strain, a *L. anisa* strain, a *L. sainthelensi* strain, a *L. bozemanii* strain, a *L. gormanii* strain, a *L. wadsworthii* strain, and a *L. jordanis* strain.

2. The method of claim 1 wherein said modulating metabolism is inhibiting growth of said bacteria.

3. The method of claim 1 wherein said modulating metabolism is killing said bacteria.

4. The method of claim 1 wherein said contacting said bacteria comprises the further step of introducing said composition into a mammal.

5. A method of treating or preventing a bacterial infection by atypical upper respiratory pathogenic bacteria comprising the step of administering an antibacterially effective amount of a composition comprising a gemifloxacin compound, or an antibacterially effective derivative thereof, to a mammal suspected of having or being at risk of having an infection with atypical upper respiratory pathogenic bacteria, and wherein said atypical upper respiratory pathogenic bacteria is selected from the group consisting of: a *L. dumoffii* strain, a *L. longbeacheae* strain, a *L. micdadei* strain, a *L. oakridgensis* strain, a *L. feelei* strain, a *L. anisa* strain, a *L. sainthelensi* strain, a *L. bozemanii* strain, a *L. gormanii* strain, a *L. wadsworthii* strain, and a *L. jordanis* strain.

6. The method of claim 1 or 5 wherein said contacting is performed once daily.

7. The method according to claim 1 or 5 wherein the gemifloxacin compound is gemifloxacin or a pharmaceutically acceptable salt thereof.

8. The method according to claim 7 wherein the gemifloxacin compound is gemifloxacin mesylate or a hydrate thereof.

9. The method according to claim 8 wherein the gemifloxacin compound is gemifloxacin mesylate sesquihydrate.

* * * * *

UNITED STATES PATENT AND TRADEMARK OFFICE
CERTIFICATE OF CORRECTION

PATENT NO. : 6,340,689 B1 Page 1 of 1
DATED : January 22, 2002
INVENTOR(S) : Jacques Dubois and Claude St-Pierre It is certified that error appears in the above-identified patent and that said Letters Patent is hereby corrected as shown below:

<u>Column 12,</u>
Line 48, "pathogexnic" should read -- pathogenic --

Signed and Sealed this

Eighteenth Day of June, 2002

*Attest:*

*Attesting Officer*

JAMES E. ROGAN
*Director of the United States Patent and Trademark Office*